United States Patent
Landsman et al.

(10) Patent No.: US 9,925,450 B2
(45) Date of Patent: Mar. 27, 2018

(54) DEVICE TO PRECISELY ALIGN GOLF CLUB FACE TO TARGET

(71) Applicants: Stephen Phillip Landsman, Pikesville, MD (US); Richard Norwood Conrey, Marriottsville, MD (US)

(72) Inventors: Stephen Phillip Landsman, Pikesville, MD (US); Richard Norwood Conrey, Marriottsville, MD (US)

( * ) Notice: Subject to any disclaimer, the term of this patent is extended or adjusted under 35 U.S.C. 154(b) by 0 days.

(21) Appl. No.: 15/603,983

(22) Filed: May 24, 2017

(65) Prior Publication Data

US 2017/0368438 A1    Dec. 28, 2017

Related U.S. Application Data

(60) Provisional application No. 62/355,609, filed on Jun. 28, 2016.

(51) Int. Cl.
*A63B 69/36* (2006.01)
*A63B 71/06* (2006.01)

(52) U.S. Cl.
CPC ...... *A63B 69/3608* (2013.01); *A63B 69/3632* (2013.01); *A63B 71/0622* (2013.01); *A63B 2071/0625* (2013.01); *A63B 2209/08* (2013.01); *A63B 2220/12* (2013.01); *A63B 2220/16* (2013.01); *A63B 2220/18* (2013.01); *A63B 2220/836* (2013.01)

(58) Field of Classification Search
USPC ....... 473/199, 209, 210, 212, 215, 220, 223, 473/403, 407, 409
See application file for complete search history.

(56) References Cited

U.S. PATENT DOCUMENTS

| | | | | |
|---|---|---|---|---|
| 6,050,963 | A * | 4/2000 | Johnson | A61B 5/1124 600/587 |
| 7,101,287 | B1 * | 9/2006 | Wagner | A63B 69/3608 473/151 |
| 7,780,541 | B2 * | 8/2010 | Bauer | A61B 5/225 2/161.2 |
| 9,301,563 | B2 * | 4/2016 | Hardy | A41D 19/0031 |
| 9,393,477 | B2 * | 7/2016 | Landsman | A63B 69/3608 |
| 2002/0173364 | A1 * | 11/2002 | Boscha | A63B 69/3617 473/131 |
| 2010/0222152 | A1 * | 9/2010 | Jaekel | A63B 69/3617 473/223 |
| 2011/0224012 | A1 * | 9/2011 | Hashimoto | A63B 69/3632 473/223 |
| 2015/0375081 | A1 * | 12/2015 | Ito | G09B 19/0038 473/223 |

* cited by examiner

*Primary Examiner* — Nini Legesse
(74) *Attorney, Agent, or Firm* — Polsinelli PC

(57) ABSTRACT

A system for correcting alignment of a golf club is provided. The golf club includes a shaft, a golf club head mounted on a first end of the shaft, a camera embedded in the golf club head. A display module is adapted to display at least a partial view of the camera. Substantial alignment of a face of the golf club head with a target location will be observable in the display as substantial alignment between the target location with an alignment guide. Misalignment of a face of the golf club head with the target location will be observable in the display as a misalignment between the target location with the alignment guide, for which a position of the golf club can be adjusted to bring the face of the golf club head into substantial alignment with the target location.

17 Claims, 18 Drawing Sheets

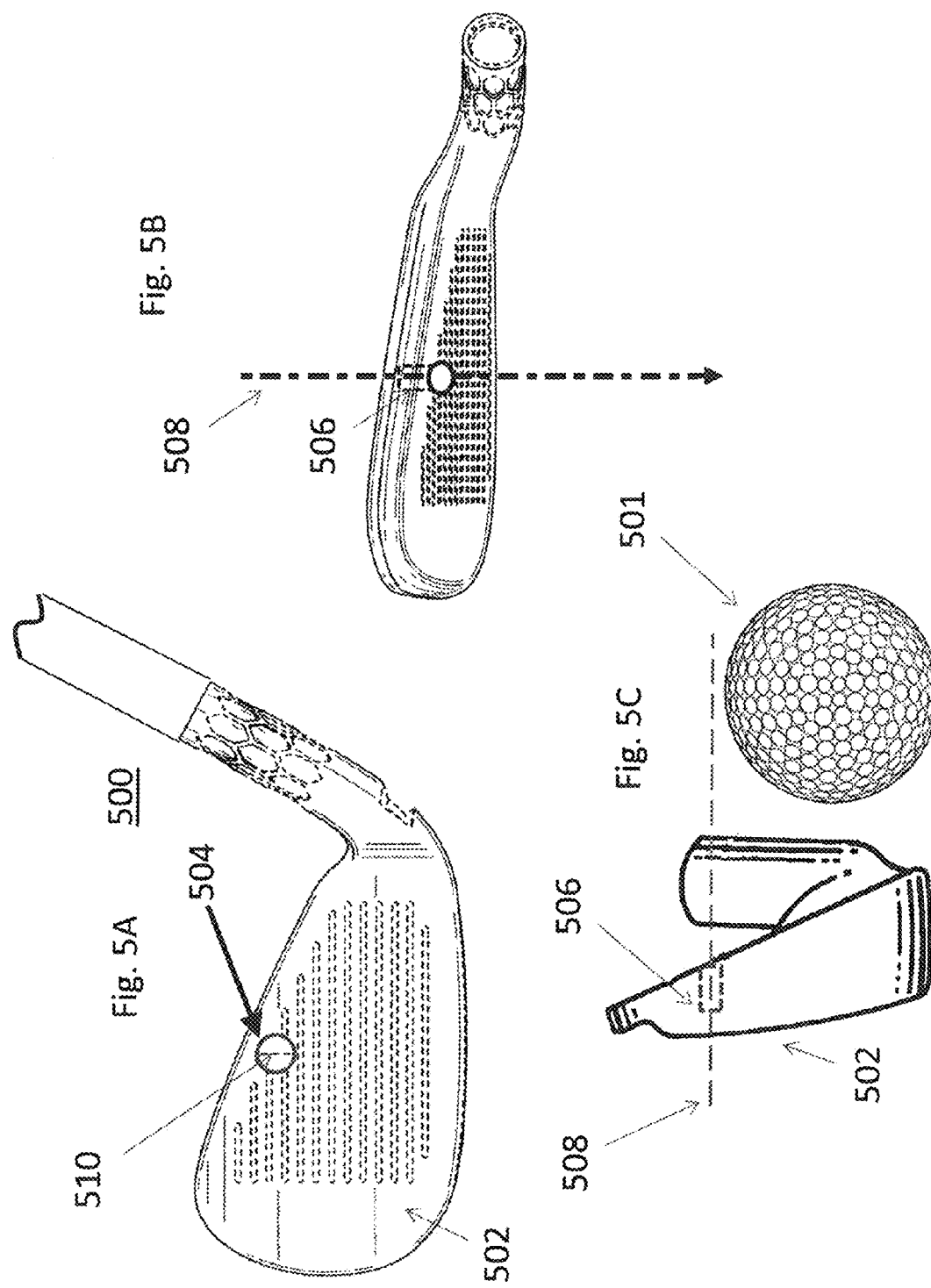

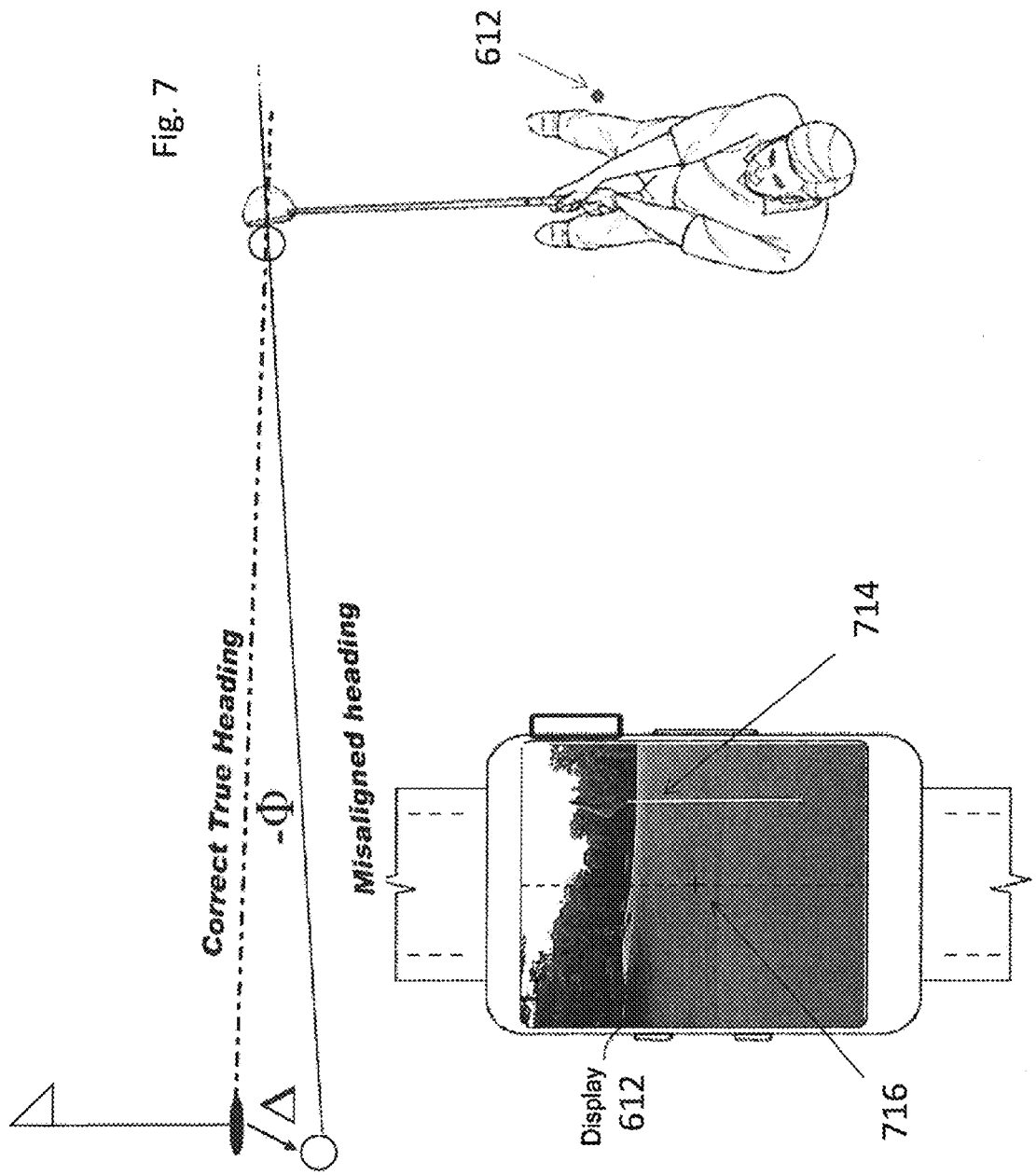

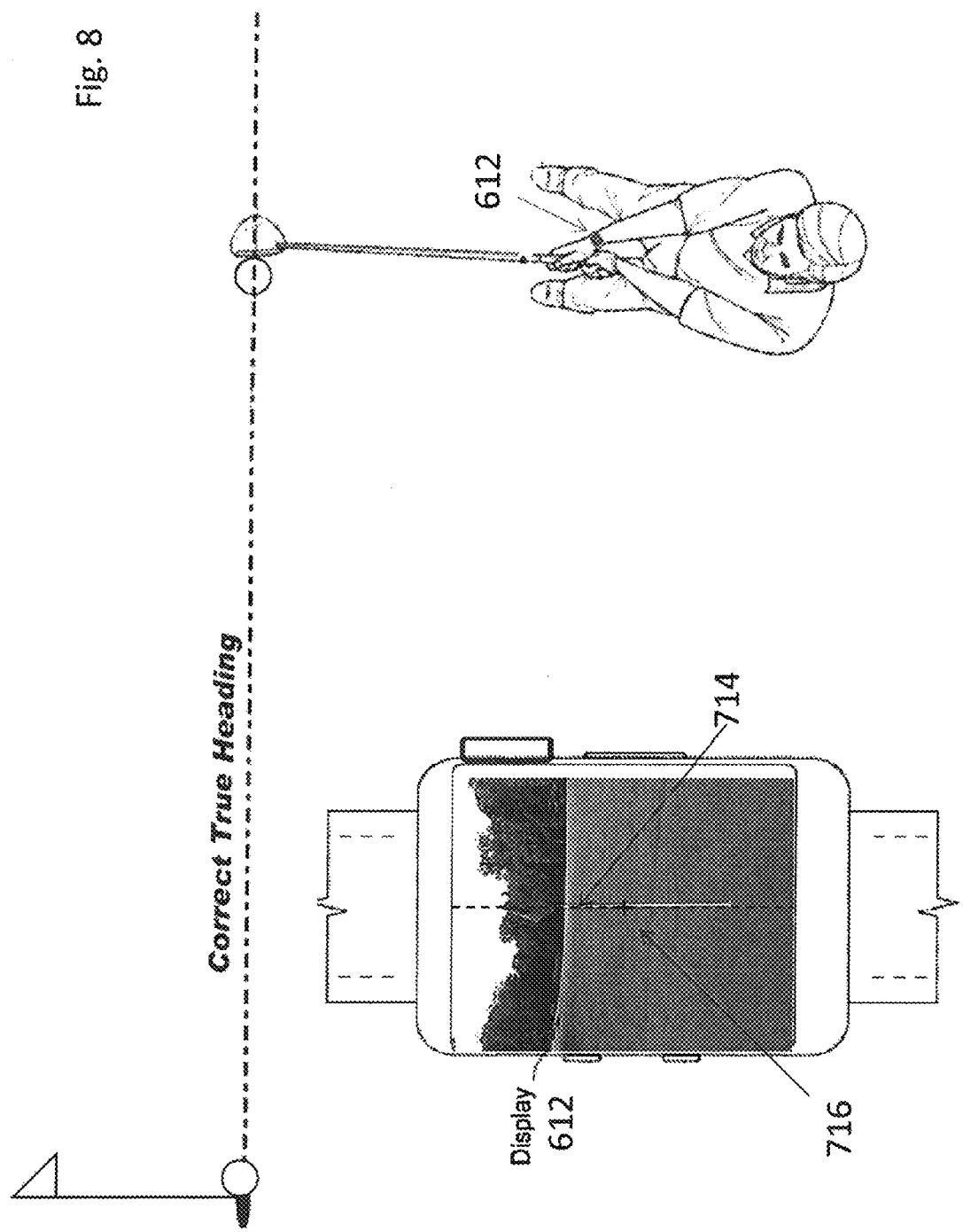

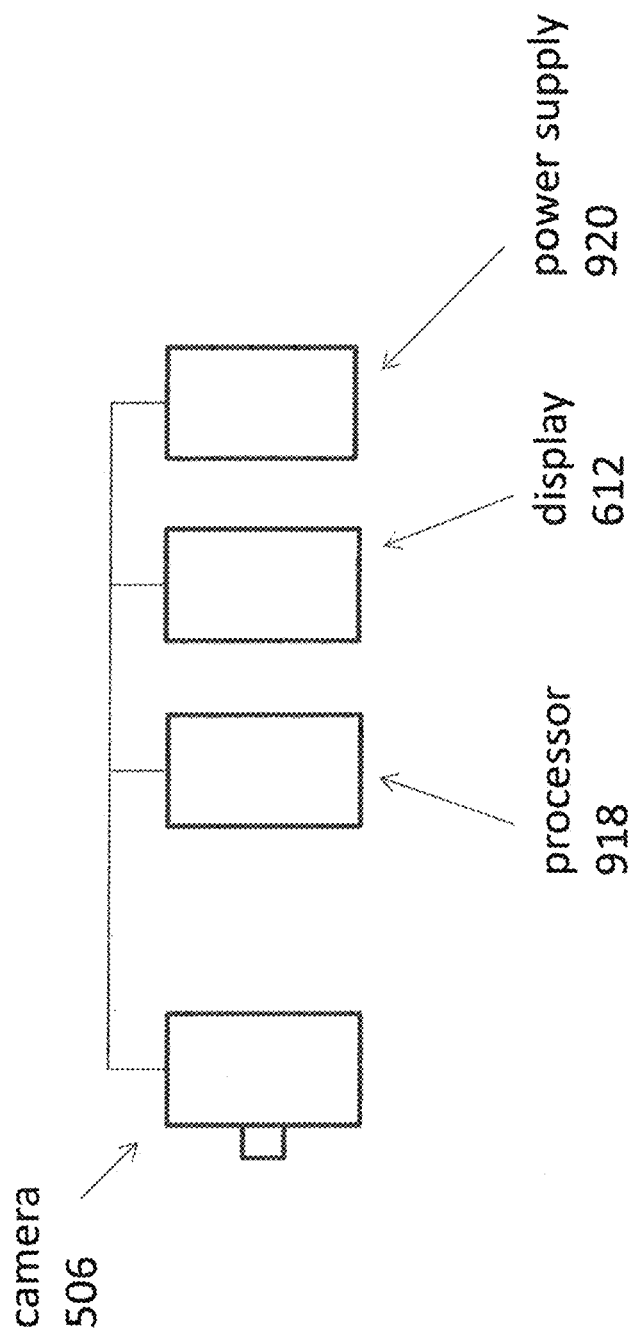

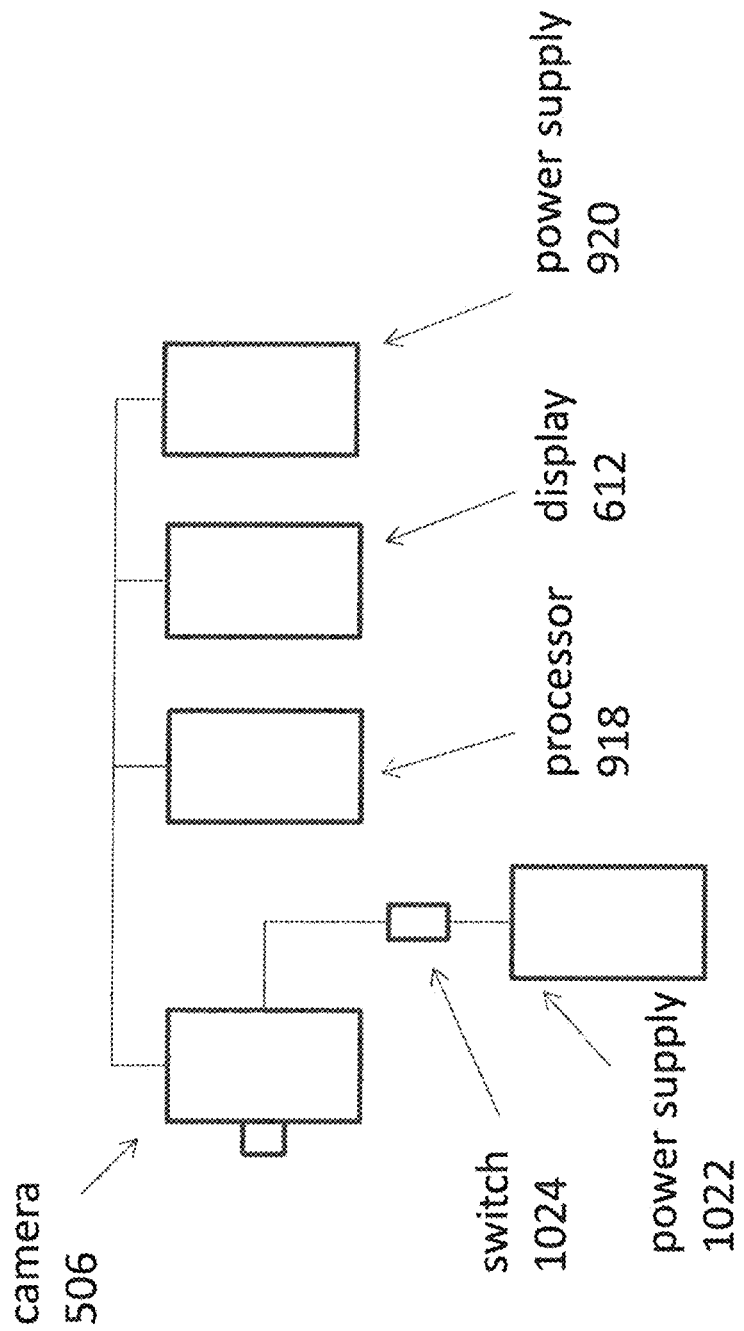

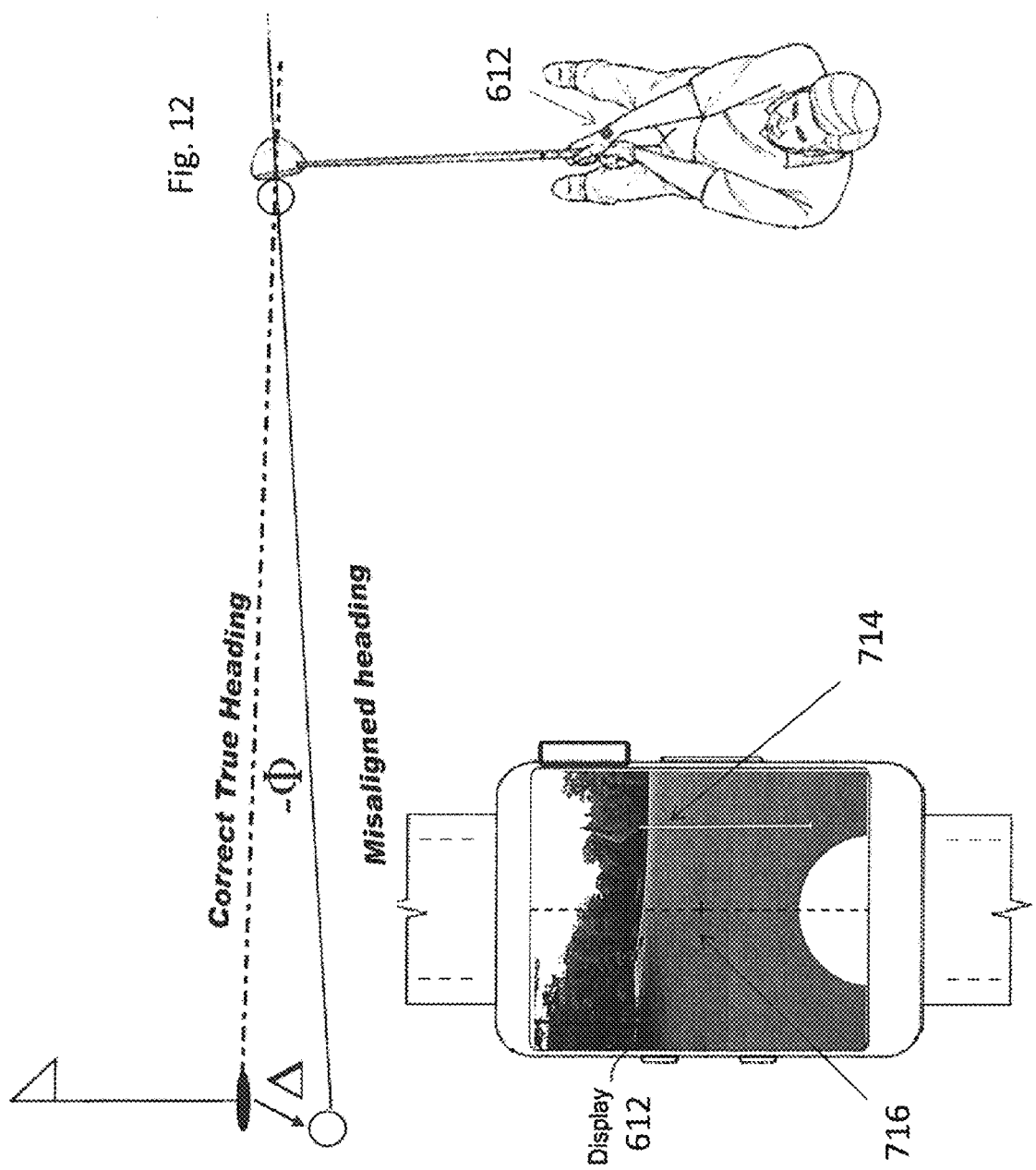

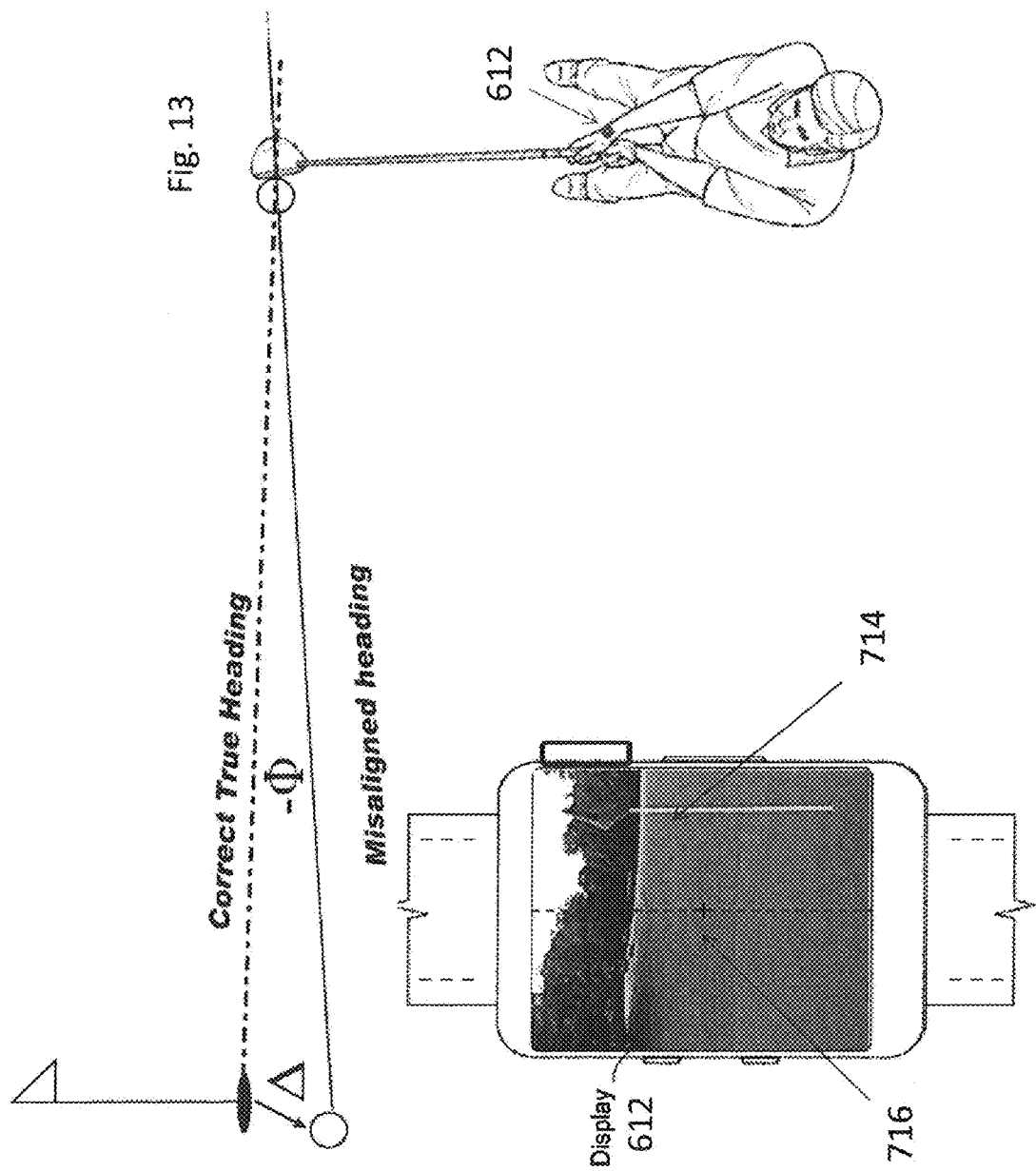

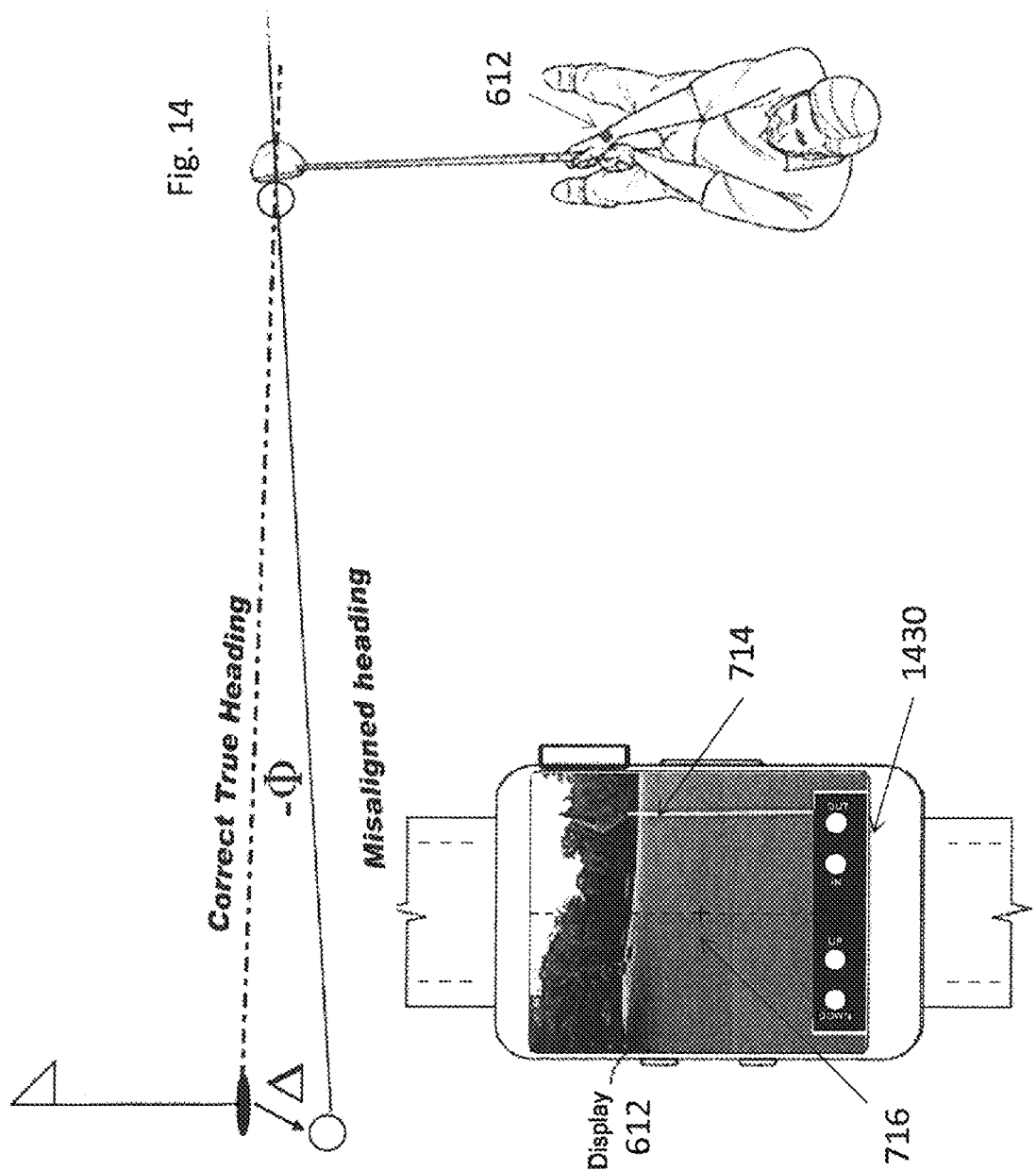

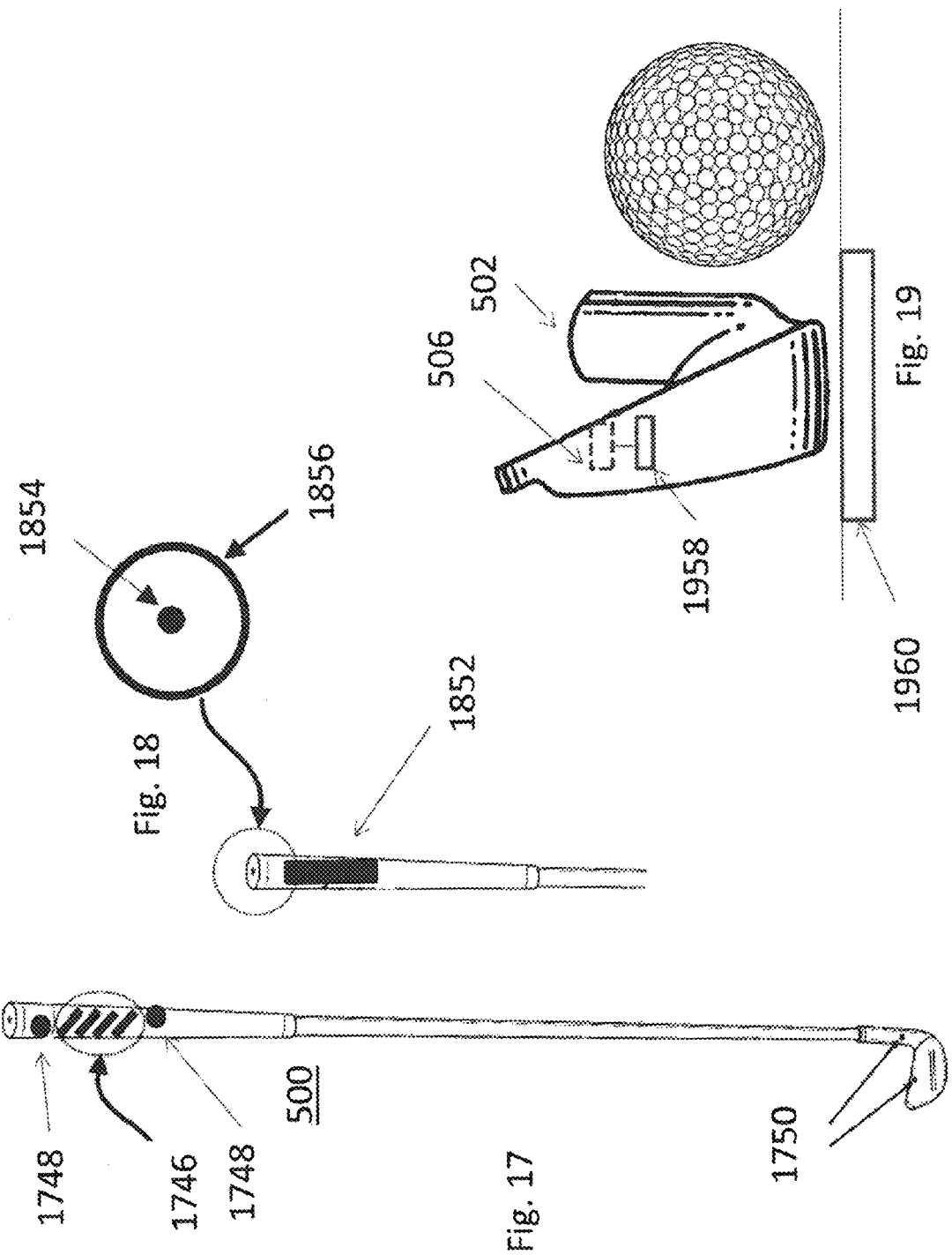

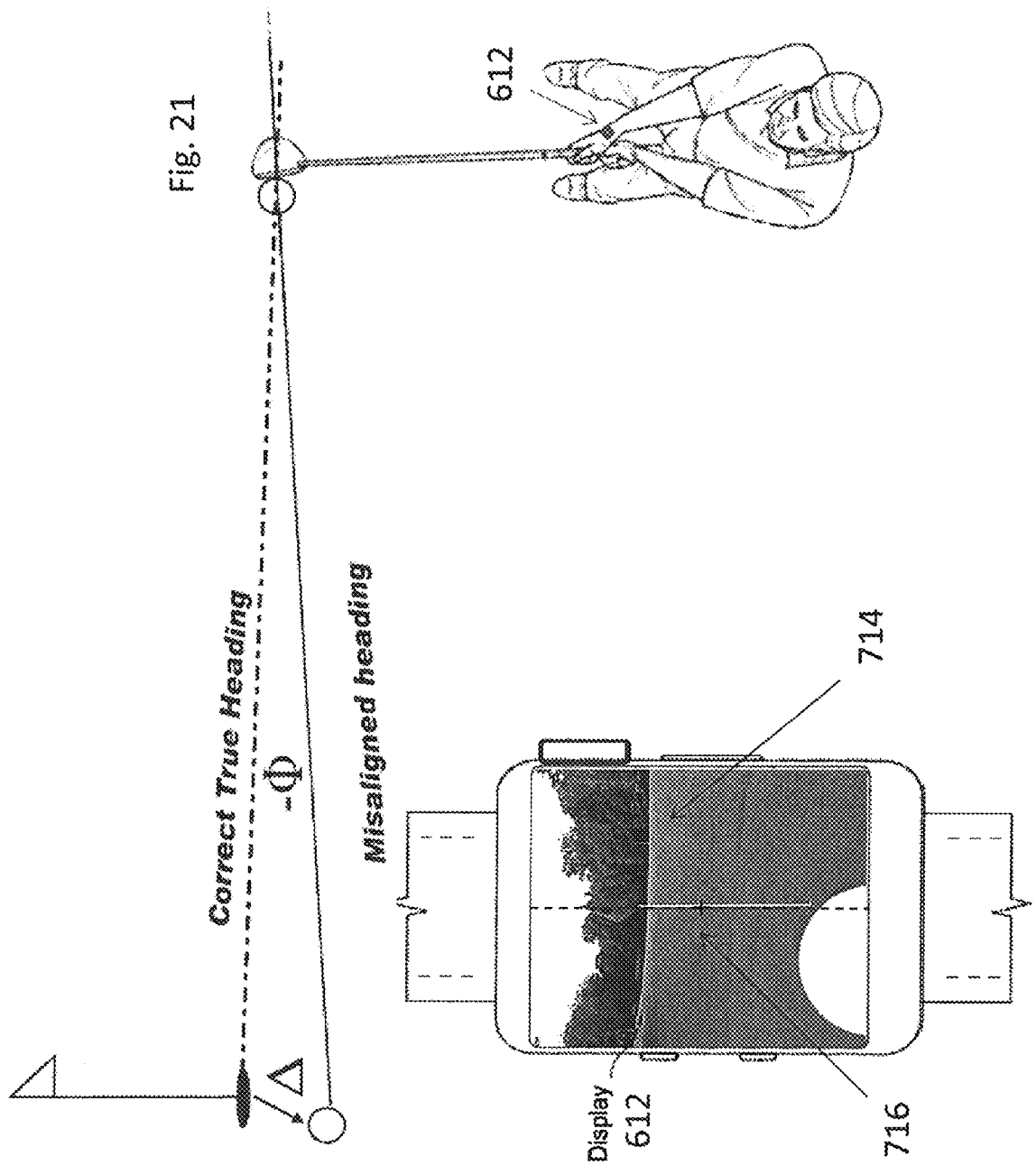

DEVICE TO PRECISELY ALIGN GOLF CLUB FACE TO TARGET

CROSS REFERENCE TO RELATED APPLICATIONS

The various instant application claims priority to U.S. Patent Application 62/355,609 entitled Device to Precisely Align Golf Club Face to Target, filed on Jun. 28, 2016, the contents of which are expressly incorporated by reference herein in its entirety.

FIELD OF THE INVENTION

The present invention relates to a golfing aid. More specifically, the present invention relates to a golfing aid that provides a visual alignment guide for the golfer to properly orient his club face and body relative to optimal swing path for a golf ball.

BACKGROUND

The game of golf is primarily accuracy based. Referring now to FIG. 1, ultimately the golfer 100 wants to strike a ball 102 and have it land at a target point 104, which may be the pin 106. For ease of discussion, the pin 106 is considered herein as the target point, although it is to be understood that this need not be the case.

Ideally (in optimal weather conditions) the golfer wants to strike the ball along an imaginary straight line drawn from the ball 102 to the target point 104, referred to herein as the "correct true heading". When the golfer strikes the ball squarely along that line with a stroke exactly coincident to that line at time of impact, the trajectory towards target is optimized for that path in still weather conditions.

A methodology for aligning the body with the ball is often referred to as the "railroad tracks". The golfer approximates or judges the correct true heading, which acts as one rail of the railroad tracks. The golfer then aligns the forward ends of his feet in parallel with the selected heading, which acts as the other rail of the railroad tracks. The hands are then placed in optimal position on the club, with the hand facing the ball preferably perpendicular to the correct true heading. FIG. 2 shows the correct orientation of the golfer relative to a particular shot. If correctly aligned, the strike path of the ball 102 to the target point 104 is optimized for that path.

Referring now to FIGS. 3 and 4, a drawback of the above methodology is that any misalignment will cause the ball strike path to deviate from the target point 104. Misalignment may come from, inter alia, a poor judgment/approximation of the correct true heading, misalignment of the golfer's feet relative to parallel with the correct true heading, misalignment of the golfer's hand relative to the perpendicular to the correct true heading, etc. At 100 yards between the ball 102 and the target point 104, one (1) degree of misalignment translates to over five feet of lateral deviation from the intended landing point, and upwards of eight feet at 150 yards.

BRIEF DESCRIPTION OF THE DRAWINGS

Various embodiments in accordance with the present disclosure will be described with reference to the drawings, in which:

FIGS. 5A-C are front, top, and side views according to an embodiment of the invention.

FIG. 7 illustrates a view on the display module when the golf club is misaligned with the target point according to an embodiment of the invention.

FIG. 8 illustrates a view on the display module when the golf club is aligned with the target point according to an embodiment of the invention.

FIGS. 9-11 are schematics of the electronics in a golf club according to embodiment of the inventions.

FIG. 12 illustrates a view on the display module when the golf club is misaligned with the target point according to an embodiment of the invention.

FIG. 13 illustrates a view on the display module when the golf club is misaligned with the target point and the view is zoomed in according to an embodiment of the invention.

FIG. 14 illustrates a view on the display module when the golf club is misaligned with the target point according to an embodiment of the invention.

FIGS. 17 and 18 are views of a golf club according to various embodiments of the invention.

FIG. 19 is a side view of a golf club and external power supply according to an embodiment of the invention.

FIG. 21 illustrates a view on the display module when the golf club is aligned with the target point but misaligned with the ball according to an embodiment of the invention.

DETAILED DESCRIPTION

Figure 1:
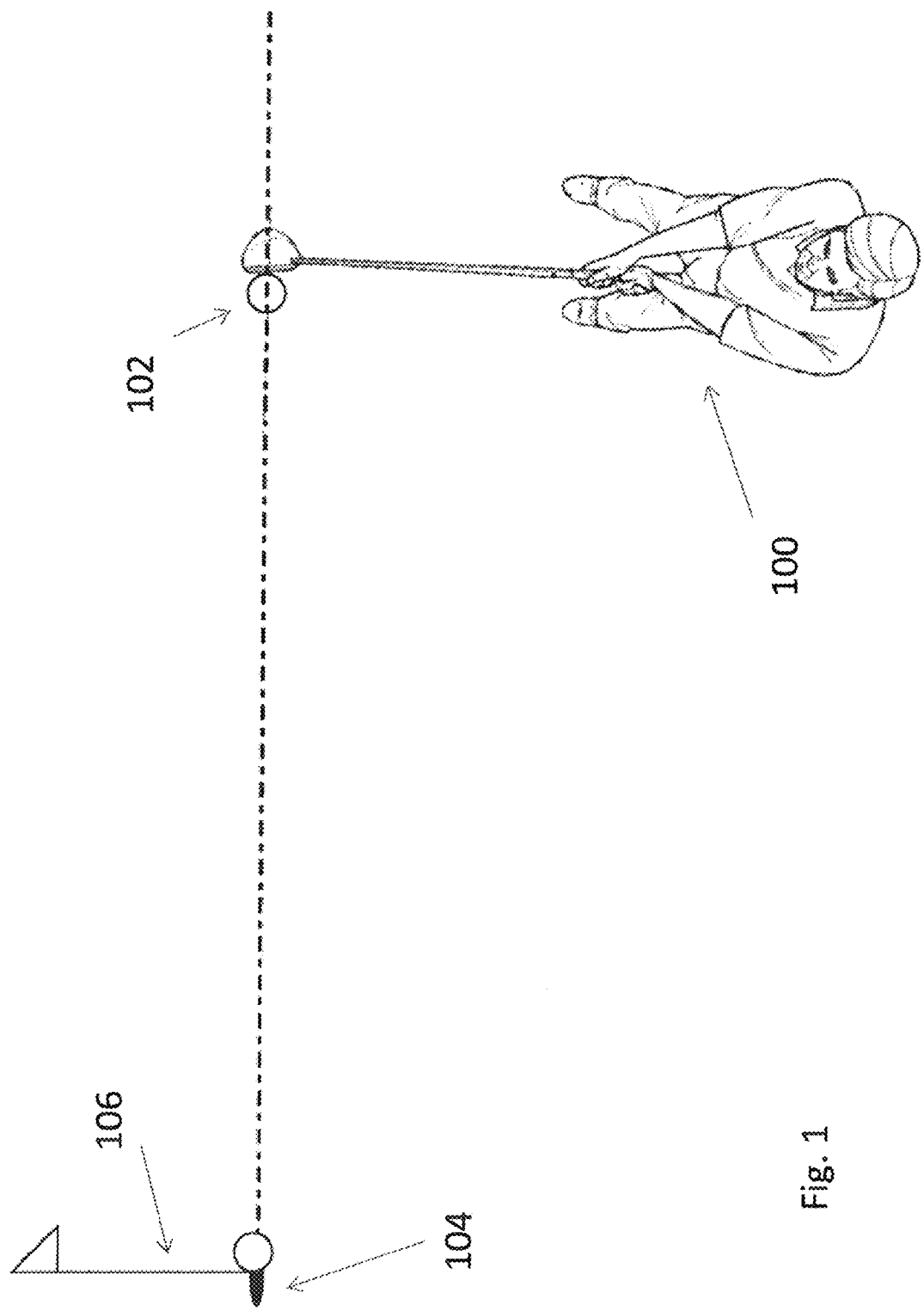
FIGS. 1 and 2 illustrate a desired proper alignment between a golf club and a target point.
Figure 2:
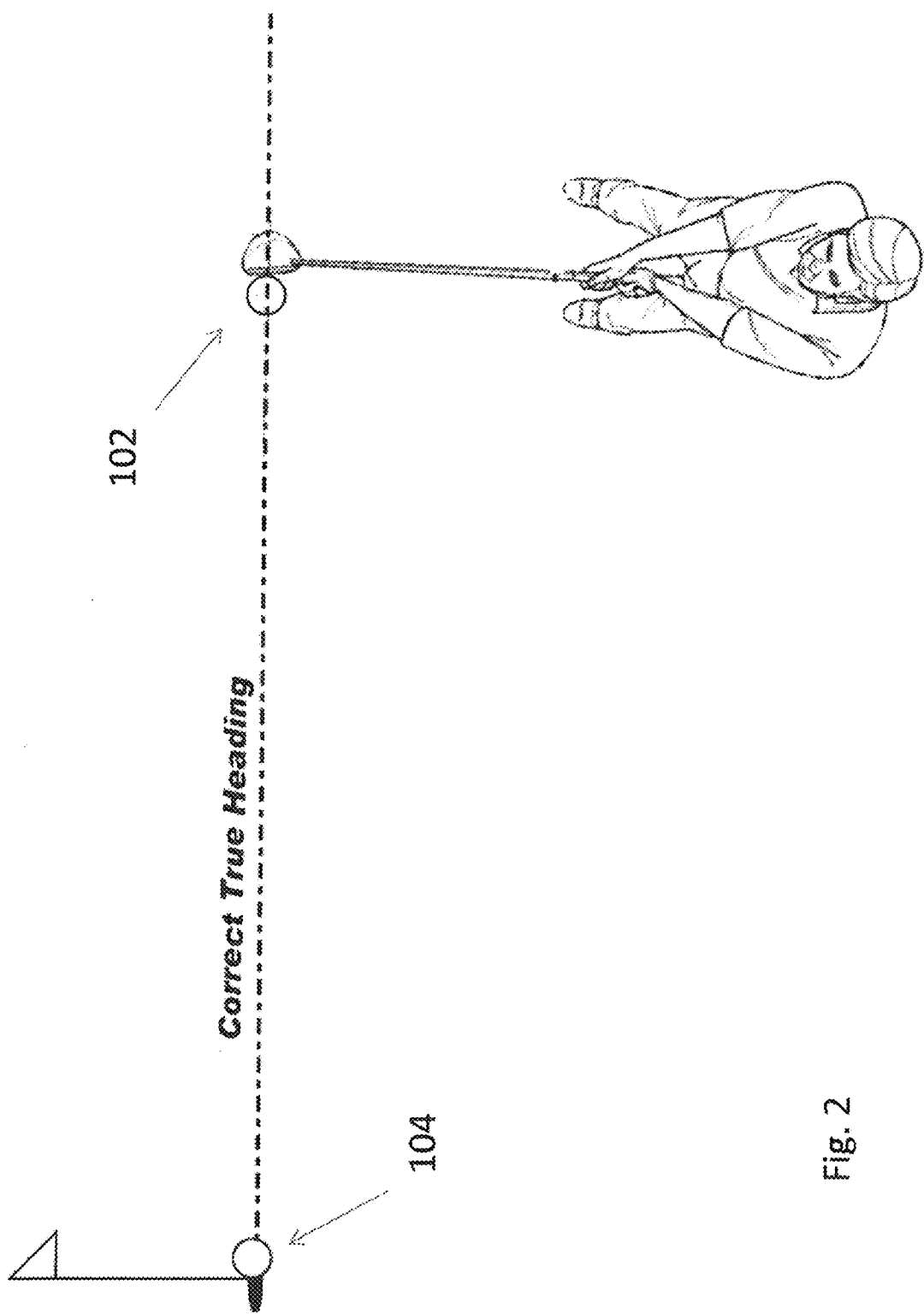
Figure 3:
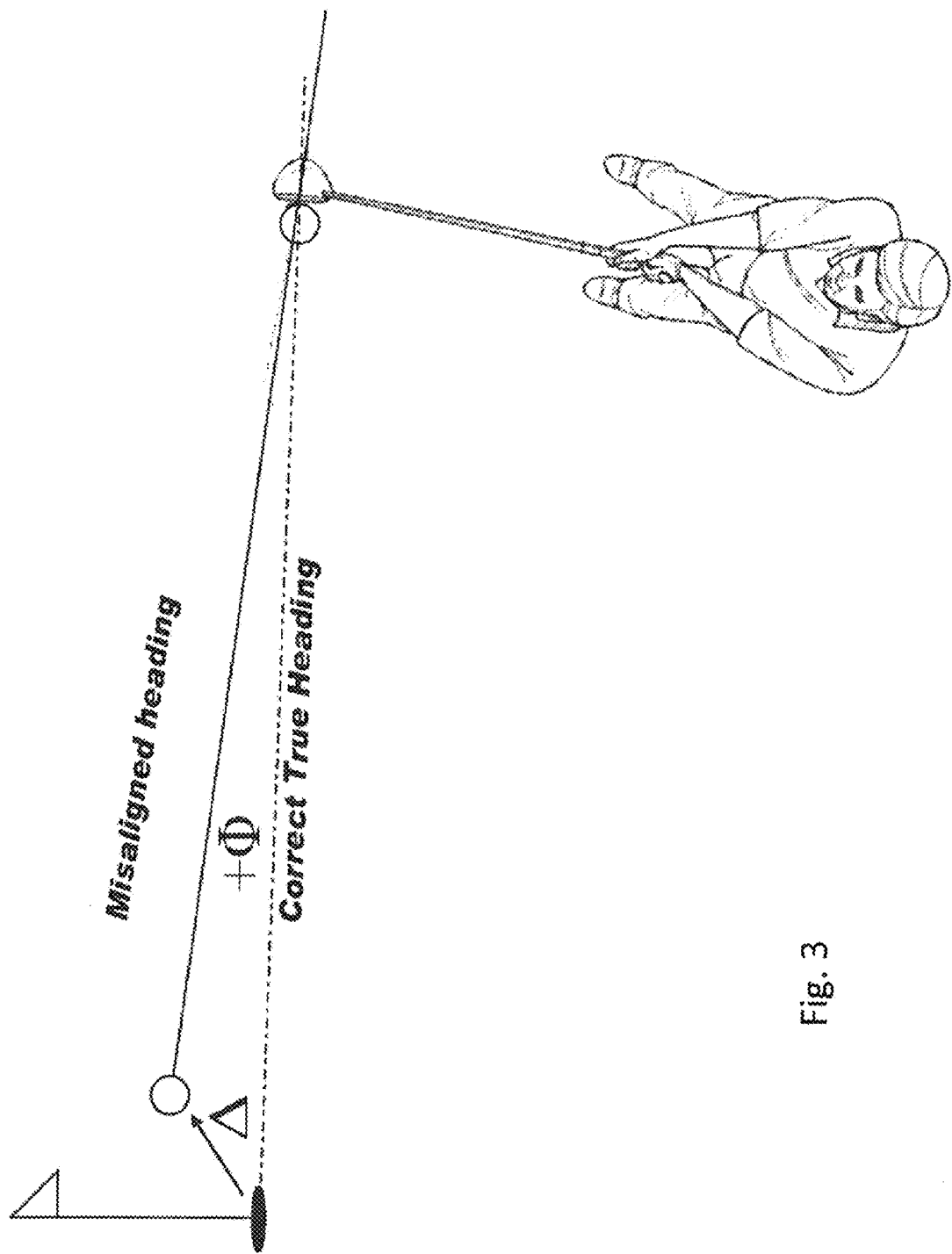
FIGS. 3 and 4 illustrate various misalignments between the golf club and the target point.
Figure 4:
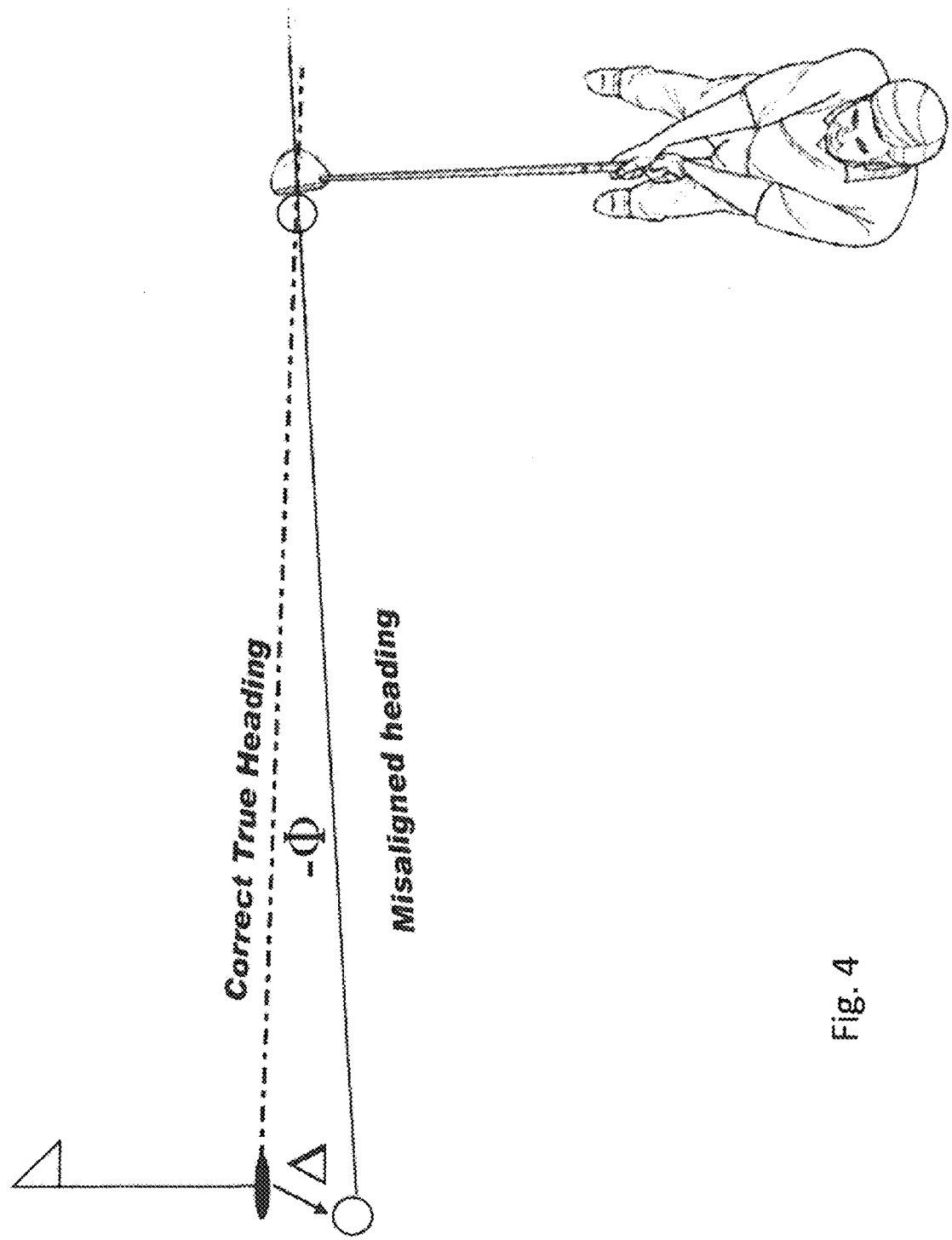

In the following description, various embodiments will be illustrated by way of example and not by way of limitation in the figures of the accompanying drawings. References to various embodiments in this disclosure are not necessarily to the same embodiment, and such references mean at least one. While specific implementations and other details are discussed, it is to be understood that this is done for illustrative purposes only. An individual skilled in the relevant art will recognize that other components and configurations may be used without departing from the scope and spirit of the claimed subject matter.

Several definitions that apply throughout this disclosure will now be presented. The term "substantially" is defined to be essentially conforming to the particular dimension, shape, or other feature that the term modifies, such that the component need not be exact. For example, "substantially cylindrical" means that the object resembles a cylinder, but can have one or more deviations from a true cylinder. The term "comprising" when utilized, means "including, but not necessarily limited to"; it specifically indicates open-ended inclusion or membership in the so-described combination, group, series and the like. The term "a" means "one or more" absent express indication that it is limited to the singular. "First," "second," etc. are labels to differentiate like terms from each other, and does not imply any order or numerical limitation.

Embodiments herein are directed to adjusting the face of a golf club relative to a target point so that the club face is aligned with the target point. However, it is to be understood that such alignment is based on a person supporting a suspended object (golf club head) and will be subject to some degree of motion. Alignment will thus never be perfect as in the mechanical sense, but are subject to human error and corresponding deviations of human movement. Discussions of alignment herein are to be understood as being modified by "substantially" whether or not expressly stated to account for such human movement. Non-limiting examples of substantial alignment at 100 yards includes less than or equal to 0.3 degrees, preferably less than or equal to 0.2 degrees, and particularly less than or equal to 0.1 degrees.

It is to be understood that the target point is an arbitrary point in space that the golfer elects to align with, essentially a reference that combined with the position of the golf club head establishes a direction. The target point may or may not correspond to a physical object, and if an object may not correspond to an actual target destination of the ball. For example, a flag pin at short range could be a target point, but at 600 yards is simply relied upon for alignment purposes (being out of range). A location in the sky may be a target point if it defines with the golf club a direction of desired ball travel.

Referring now to FIGS. 5A-5C, a first embodiment of the invention is shown. The embodiment includes a golf club 500 having a golf club head 502. A video camera is mounted in recess 504 in golf club head 502 at or proximate to the optimal strike point of the head 502, preferably as shown in FIG. 5C above the height of the golf ball 501 when the club head 502 is in striking position. The view of the camera 506 thus reflects the view of the playing area from the perspective of golf club head 502. Camera 506 is preferably installed in head 502 such that the optical axis 508 of camera 506 is parallel to the bottom base of the club on a horizontal plane, although the invention is not so limited. An alignment marker 510, such as a reticle, may be provided in camera 506 (e.g., etched into the lens).

Figure 6B:
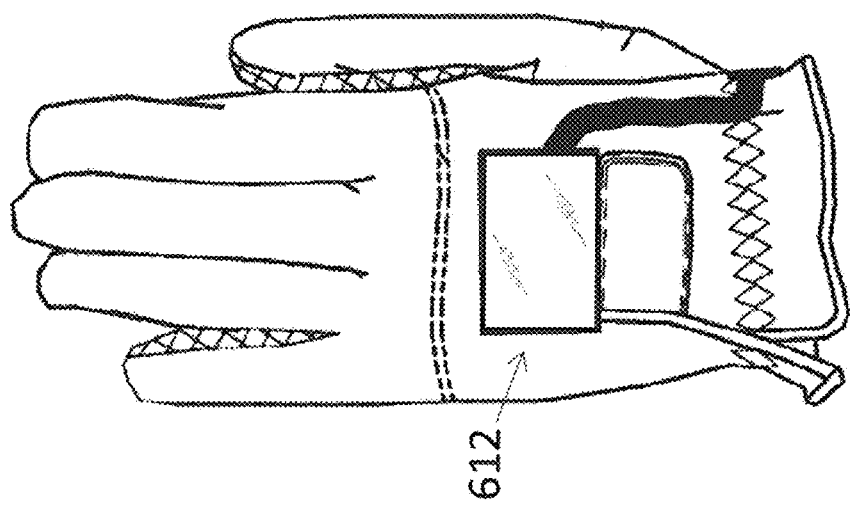
FIGS. 6A and 6B are embodiments of a display module according to an embodiment of the invention.
Figure 6A:
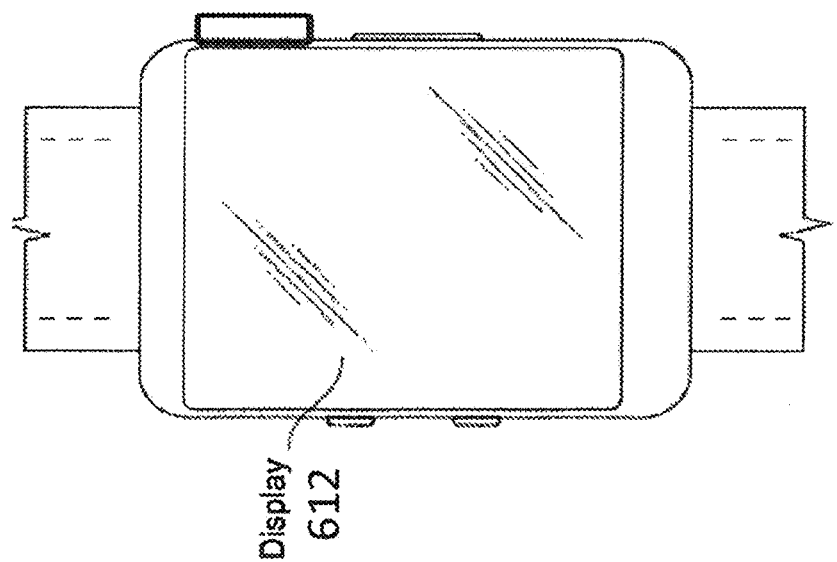

Referring now to FIGS. 6A and 6B, golf club 500 operates in conjunction with a display 612 which shows what is observed by camera 506. Display 612 is preferably mounted in body worn component such as a wrist worn device (e.g., APPLE WATCH) as in FIG. 6A or on a glove as shown in FIG. 6B. However, in the invention is not so limited, and other locations (body worn or not) may also be used. By way of non-limiting example, it could be part of glasses (e.g., GOOGLE GLASS), placed on the club handle, or simply leverage the features of a typical smartphone.

FIGS. 7 and 8 demonstrate the methodology of aligning a golf club. In FIG. 7, the golfer will take their golfing stance in a normal manner, using best judgment to align the face of the golf club head to strike the ball to reach the desired target point 714, in this case the pin. Despite the golfer's best judgment, as shown in the FIG. 7 the golfer is misaligned with the target point 714 by an angle $-\Phi$, such that if the ball is struck perfectly under ideal wind conditions the ball would tend to land off to the left of the pin (although other factors will likely contribute to the ultimate landing point).

In this case, before swinging the golfer can identify any misalignment by observing the display 612 to see if the target point 714 is aligned with the center of display 612, which is this embodiment that is indicted by a marker 716. In FIG. 7, the golfer can observe in display 612 that the target point 714 is misaligned with marker 716, which in turn means that golf club 500 is not in the proper alignment. Referring now to FIG. 8, the golfer can respond by repositioning any aspect of their stance to bring the target point 714 into substantial alignment with the marker 716. Striking the ball in this position would yield results consistent with near perfect alignment of the golf club face with the target point. This realignment may be anything as simple as rotating the golf club 500 to compensate to an entire reset of the stance. The invention is not limited to the manner in which the golfer moves to establish proper alignment to bring the target point 714 into substantial alignment with the marker 716.

Marker 716 may be provided to identify the center a display 612, such as by marker 510 as observed by camera 506, a separate physical marker on display 612, and/or a marker added via the underlying image software. The invention is not limited to the manner in which marker 714 is provided. In the alternative no marker may be provided.

To the extent that the ball 501 is visible in display 612, then the system may also allow the golfer to observe and correct for a misalignment between the club 500 and the ball 501. Specifically, when the ball is properly aligned the top of the ball would align with the center of display 612; marker 714 (if present) would thus align with the top of the ball as shown in FIG. 12. If the marker 714 is aligned with another portion of the ball 501, then the golfer could observe the same such as in FIG. 21.

The instant embodiment can serve as either a training golf club or an actual golf club for course use. The training option would show the golfer misalignments due to errors in judgment, e.g., the golfer perceives they are aligned when in fact they are not; via practice the golfer can improve their judgment of alignment accuracy without even striking the ball. The actual option is to use the golf club as an actual play club on the course.

System architecture may be based on wired or wireless principles. Referring now to FIG. 9, a schematic of a wired based embodiment of the system is shown for a wired implementation. Components of the golf club 500 include camera 506 and supporting circuitry. Components of the display end include display 612, a processor 918, and a power supply 920 (which may be a common power source or separate power sources, including distinct power sources for the electrical components in golf club 500 components).

As discussed in more detail below, in this embodiment the power pathway from power supply 920 to the electrical components in golf club head is via physical contact between the golfer and the club, such that the components are OFF when the club is not held; no switch is therefore necessary, although one may nonetheless be provided.

FIG. 10 shows another wired embodiment in which a power supply 1022 powers the golf club 500 components independently as part of golf club 500. A non-limiting example of such a power supply is batteries, preferably placed in the shaft near the grip to minimize impact on the balance of the club. Another example is a magnetic inductive power supply that receives power from an external inductive source; this option may be preferable for training clubs in a predefined practice area, in which practice area has built in cables underneath the practice area that would generate electromagnetic fields that could be picked up by a receiver in the golf club 500 and transformed into electric power. This option potential may prove more effective for club that are made from non-ferrous materials to avoid interference.

A switch 1024 may be provided relative to the power supply 1022 and the electrical components of golf club 500 to turn off the power when the club is not in use. Switch 1024 may be a simple manually actuable ON/OFF, although preferably is reactive to the circumstances of use, such as responsive to the orientation of the club 500 (in striking position for ON, and OFF when laying down or inverted in the golf bag) and/or a pressure switch responsive to the club bring gripped. The system is not limited to the nature of the switch used.

Figure 11:
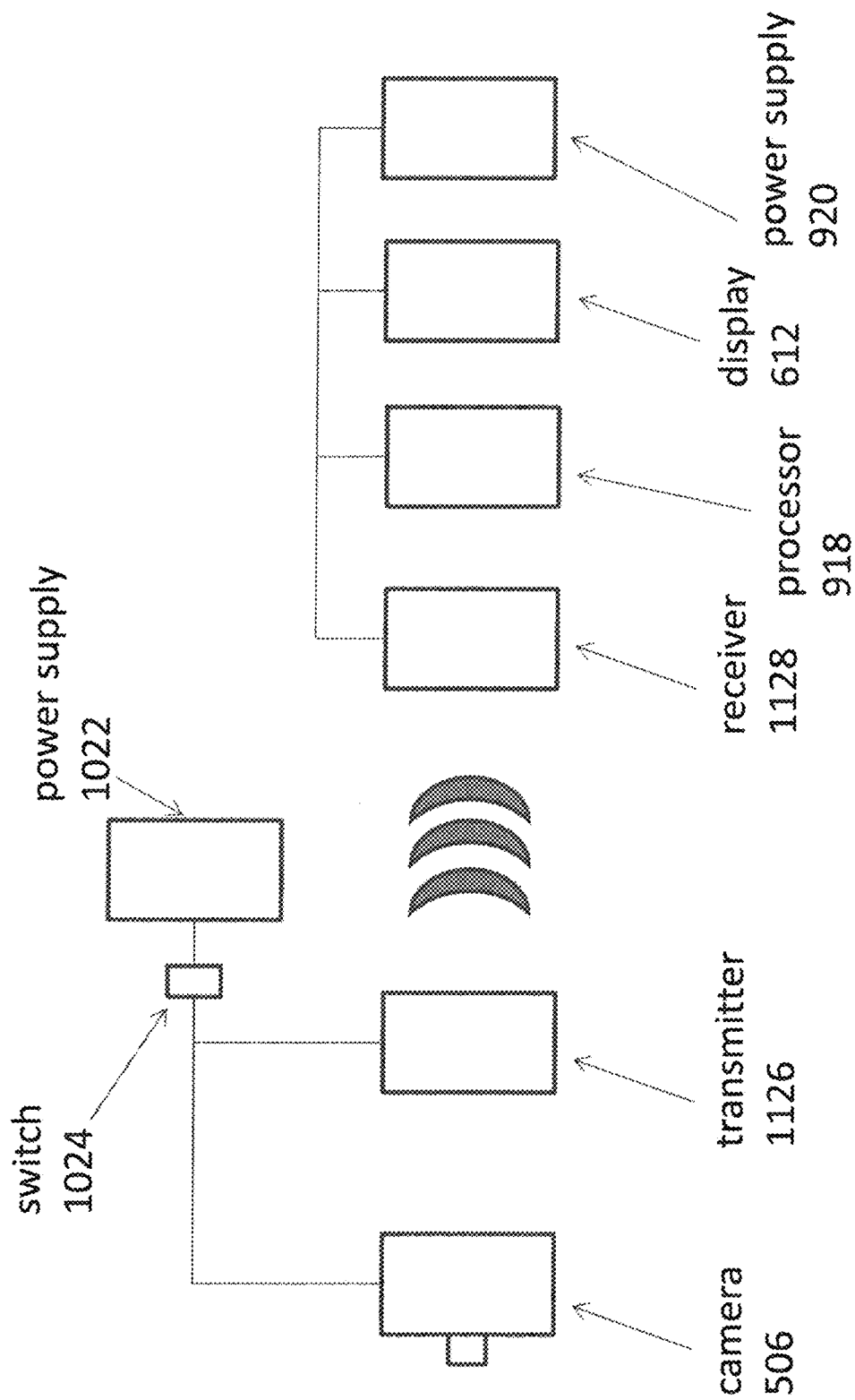

FIG. 11 shows an example of a wireless embodiment. The architecture is similar to FIG. 10, although a wireless transmitter 1126 and a wireless receiver 1128 are also provided to transmit video data from camera 612. Transmitter 1126 and wireless receiver 1128 are preferably adapted for BLUETOOTH or 802.11 communications, although the invention is not so limited and any other appropriate transmitter/receiver may be used.

The methodology may rely upon certain software and/or hardware features to enhance the information and experience provided by some or all of the various embodiments herein. For example, referring to FIG. 12, the ball 501 may lie in the field of view of camera 506 and thus appear on display 612. An embodiment of the system can change the picture to remove all or part of the ball 501. By way of non-limiting example, the system can digitally zoom in or crop to partially or completely eliminate the ball 510 from the display content, such as shown in FIG. 13. The amount of zoom could be preset, or the software could be programmed to detect the presence of the ball 501 and to zoom until the desired amount of the ball 501 is removed from the image. In addition and/or the alternative, referring now to FIG. 14 changes could be made on user command via a touch interface 1430 with zoom in/zoom out buttons, and/or via voice command.

The zoom functionality may also be provided simply as a convenience that is unrelated to the presence or absence of the ball 501 in the display 612. For example, the system may be preset to zoom to a certain degree, as this will allow digital manipulation of the images for other zoom, panning, tilting and/or or rotation purposes.

For example, the field of view of display 612, even when under some degree of zoom in, is typically sufficient for most playing conditions. However, there may be some extreme exceptions in which there is an interest in lowering or raising the view, for example when facing a hill that blocks the view or trying to see the top of a tree that the golfer wants to shoot over. An embodiment of the system can digitally tilt the image up or down to display different viewing angles. This could be controlled by touch interface 1430 with tin up/tilt down buttons, and/or via voice command. The zoom functionality may also be provided simply as a convenience that is unrelated to the presence or absence of the ball 501 in the display 612. Another option is to rotate the image, which may be useful if the ball is lying on in an inclined surface in which to strike the ball requires that the golf club head alignment be at an angle with the true horizon.

The underlying software and hardware to adjust the image as described herein is within the skill of those in the computer arts and are not further described herein.

Figure 16:
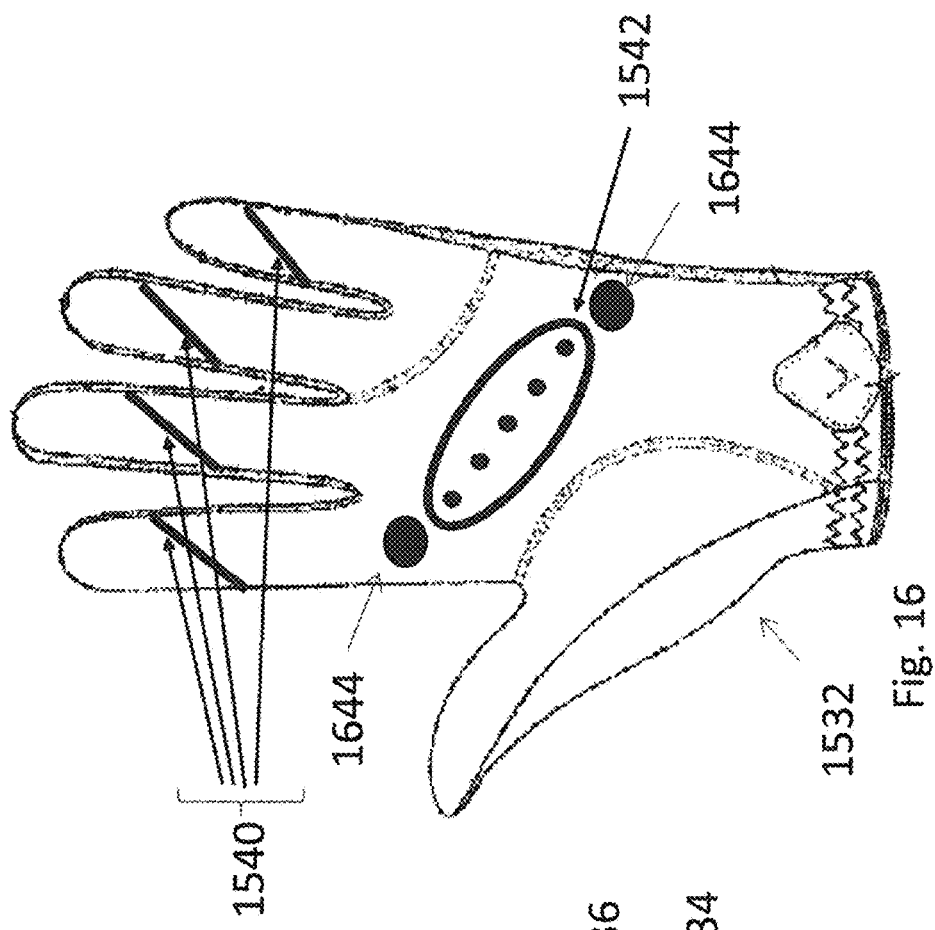
FIGS. 15 and 16 are back and front views of a glove according to an embodiment of the invention.
Figure 15:
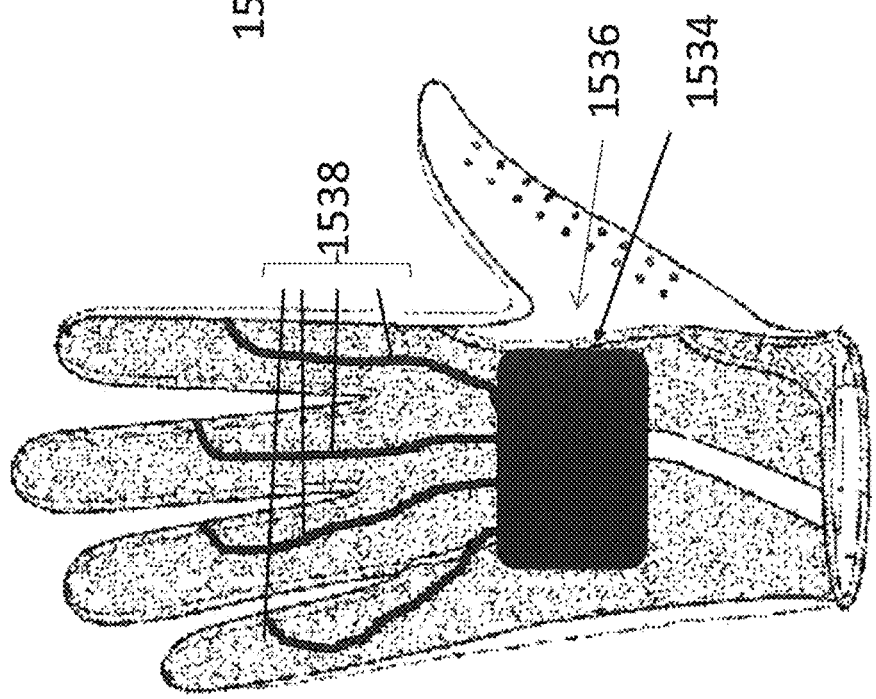

Referring now to FIGS. 15 and 16, a non-limiting example of architecture for the embodiment of FIG. 9 is shown. A glove 1532 has a module 1534 that includes display 612, processor 918 and power supply 920, along with any other typical supporting computer hardware and software as is known in the art. Module 1534 is shown centered on the back of the hand, but the invention is not limited to that placement. By way of non-limiting example, module 1534 could be placed on an area 1536 on the back of the hand relative to the thumb and forefinger, which would be easily visible to the golfer when in a standard golfing stance. Electrical pathways 1538 extend from 1534 through the glove to the front of the glove to define finger contact points 1540 and/or palm contact points 1542. FIG. 17 shows corresponding contacts 1746 on the golf club 500, which connect to camera 506 through other wires and contact paths (not shown). When the golfer grips the club 500, alignment of the various contacts creates wired electrical pathways to provide power from module 1534 to the electronics in golf club 500, and/or for the camera 506 to send video signals to module 1534. Magnets 1644 on the glove and 1748 on the grip of the shaft may be provided to ensure alignment of the contacts. The magnets 1644 may also be aligned with the contacts pads 1542 in a straight line.

Referring now to FIG. 18, a non-limiting example of architecture for the embodiment of FIG. 10 is shown. The architecture is generally the same as FIGS. 15-17, except that power source 1022 in the form of a battery 1852 is mounted in the shaft; in this embodiment the pathways 1538 (omitted in FIG. 18 for clarity) would preferably be communications/data only and not include pathways for providing power to the electronics of golf club 500. Disposable batteries could be used, in which case the top of the shaft could form the top of a battery chamber for which the top of the shaft could be removed to access. Rechargeable batteries could also be used, with terminals 1854 and 1856 serving as the charging points.

Referring now to FIG. 19, another non-limiting example of architecture for the embodiment of FIG. 10 is shown, in this case corresponding to a wireless power source. An inductor module 1958 is connected to camera 506, and an inductive power supply module 1960 that generates a magnetic field is mounted in the support golfing surface. When club head 502 is proximate to an inductive power supply module 1960, inductor module 1958 converts the magnetic field into power in a manner known in the art.

A non-limiting example of architecture for the embodiment of FIG. 11 uses a glove that is the same as 1532, save that the contact pathways and magnets are unnecessary and may be omitted. The module is the same as module 1534 save that it additionally includes receiver 1128. The golf club is the same as shown in FIG. 18 or 19, save that transmitter 1126 would also be present, preferably embedded near the top of the shaft in the grip section.

Figure 20:
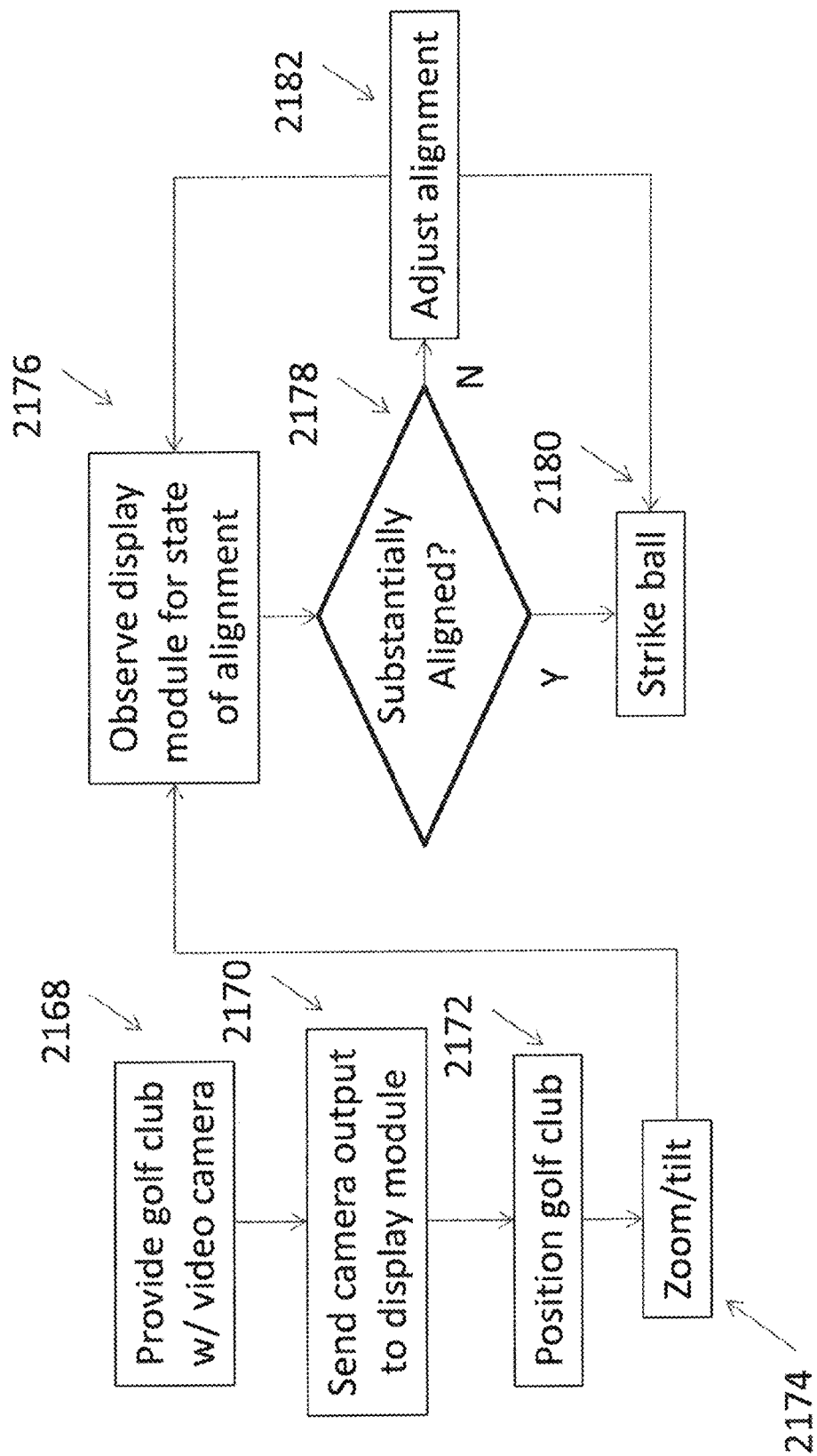
FIG. 20 is a flowchart of steps for using various embodiments of the invention.

FIG. 20 shows a method of using various embodiments described herein. At step 2168, a golf club having some or all features as described herein is provided. Output from a camera in the golf club is sent to display module at step 2170. The golfer takes the club and adopts a golfing stance to strike the ball at step 2172. Any desired zoom/tilt may be performed at step 2174. The golfer then observes the displayed image in the display module at step 2176 and judges the presence or absence of substantial alignment at step 2178. If aligned, the golfer strikes the ball at 2180. If not aligned, the golfer can adjust the alignment at 2182, and then either strike the ball or recheck alignment.

The above embodiments can reduce alignment errors between the club and the target point and reduce (if not eliminate) errors in the swing due to that misalignment.

Embodiments of the display modules herein may present an alignment guide to the golfer as a reference to indicate that the club 501 is or is not aligned with the target 714. A non-limiting example of such an alignment guide marker 716. Another example would be a colored light system relative to the degree of misalignment, such as a red color when substantially misaligned and green when substantially aligned. Yet another example would be as audio indicator.

Camera 506 is preferably any camera that is small, low power, and has sufficient image resolution and light sensitive for the task as descried herein. Non-limiting examples are CMOS or CCD cameras. However, the invention is not so limited, and any video camera may be used.

Display modules as discussed herein are shown as one-piece units that are adapted to be worn on the body, e.g., a glove or a smart watch. However, the invention is not so limited, and they may be multi-piece units that are entirely or partially adapted to be worn on the body. For example, a display module may be made from the combination of an IPHONE and APPLE WATCH, for which only the APPLE WATCH is adapted to be worn on the body.

Embodiments of the display module preferably include a memory for storing programming to effectuate the processes as set forth herein. Video from camera 506 can be captured, stored and later retrieved from such a memory for purposes of instruction, assessment or the like.

Camera 506 is preferably placed in the location shown in FIGS. 5A-5C, although the invention is not so limited. Camera 506 can be placed anywhere in golf club head 502 (including the hosel of the club head), and potentially even in the shaft. Non-limiting examples of alternative locations are shown at 1750 in FIG. 17. While in these embodiments an offset is introduced that detracts from perfect alignment, the offset is negligible and within the scope of substantial alignment as discussed herein.

Display 612 may include a cover, and the cover may act as an ON/OFF switch. The display itself may be hinged mounted on the glove or support surface so that that is can be moved from a retracted position into a more convenient deployed position to observe; the movement itself may act as ON/OFF switch where the display (and/or other system components) are OFF when the display is retracted and ON when deployed.

Various embodiments discussed or suggested herein can be implemented in a wide variety of operating environments, which in some cases can include one or more user computers, computing devices, or processing devices which can be used to operate any of a number of applications. User or client devices can include any of a number of general purpose individual computers, such as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments where the computing device includes a Web server, the Web server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, an individual of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A system for correcting alignment of a golf club, comprising:
   a shaft;
   a golf club head mounted on a first end of the shaft;
   a camera embedded in the golf club head;
   a display module, adapted to display at least a partial view of the camera;
   wherein substantial alignment of a face of the golf club head with a target location will be observable in the display as substantial alignment between the target location with an alignment guide;
   wherein a misalignment of a face of the golf club head with the target location will be observable in the display as a misalignment between the target location with the alignment guide, for which a position of the golf club can be adjusted to bring the face of the golf club head into substantial alignment with the target location.

2. The system of claim 1, wherein the display module is mounted at least partially on a glove or a wristband.

3. The system of claim 1, wherein the alignment guide comprises a physical marker in the camera, a physical marker on the display, and/or a computer generated marker on the display.

4. The system of claim 1, wherein the display module is adapted to zoom, pan, rotate and/or tilt a displayed image from the camera.

5. The system of claim 1, wherein the display module is programmed to, in response to the presence of a ball adjacent the golf club head in the field of view of the camera such that the ball at least partially appears in the displayed image, adjust a displayed image to at least partially reduce the amount of the ball appearing in the displayed image.

6. The system of claim 1, wherein the golf club further comprises a short range wireless transmitter and the display module further comprises a short range wireless receiver, wherein the camera sends video data to the display module wirelessly through the receiver and the transmitter.

7. The system of claim 1, further comprising:
   the golf club includes a plurality of first electrical contacts on a grip of the golf club, and electrical pathways extend in the shaft between the camera and the plurality of first electrical contacts;
   the display module is mounted on a glove, and the glove includes a plurality of second electrical contacts on a front of the glove, and electrical pathways extending between the display module and the plurality of second electrical contacts;
   wherein when the glove engages the grip, the first and second contacts electrically connect to permit power and/or data communication between the camera and the display module.

8. The system of claim 7, further comprising magnets on the glove and club configured to mate with each other such that the first and second electrical contacts align.

9. The system of claim 7, further comprising a power source for the camera, the power source being mounted in the second end of the shaft, wherein when the glove engages the grip, the first and second contacts electrically connect to permit data communication between the camera and the display module but not independent power.

10. The system of claim 7, wherein when the grip is not in aligned contact with the glove the camera is OFF due to the lack of power.

11. The system of claim 1, further comprising a power source for the camera, the power source being mounted in the second end of the shaft.

12. The system of claim 1, further comprising switch circuitry that turns the camera OFF, the switch circuitry including at least a tilt switch that turns the camera OFF when the golf club is in a position different from a play position consistent with being held in a golfing stance.

13. The system of claim 1, wherein the display module is mounted on the back of a glove.

14. The system of claim 1, wherein the display module is mounted on the back of a glove between the thumb and the forefinger.

15. The system of claim 1, wherein the display module includes at least a display.

16. The system of claim 1, wherein the display module include a processor and a power supply.

17. A method for correcting alignment of a golf club, comprising:
   providing a golf club, comprising:
      a shaft;
      a golf club head mounted on a first end of the shaft;
      a camera embedded in the golf club head;
   sending an output of the camera to a display module, the display being adapted to show a view of the camera;
   positioning the golf club relative to a golf ball;
   observing on the display a presence or absence of substantial alignment of a face of the golf club head with a target location by the presence or absence of substantial alignment between the target location and an alignment guide on the display module;
   adjusting, in response to the absence of substantial alignment of the face of the golf club head with a target location, the stance to improve alignment of the face of the golf club head with a target location.

* * * * *